United States Patent [19]

Burri

[11] 4,291,902
[45] Sep. 29, 1981

[54] RECORDING MATERIAL EMPLOYING SUBSTITUTED 3,6-DIAMINOPHTHALIDES AS COLOR FORMERS

[75] Inventor: Peter Burri, Reinach, Switzerland

[73] Assignee: Ciba-Geigy Corporation, Ardsley, N.Y.

[21] Appl. No.: 76,108

[22] Filed: Sep. 17, 1979

Related U.S. Application Data

[62] Division of Ser. No. 942,840, Sep. 15, 1978, Pat. No. 4,191,690.

[30] Foreign Application Priority Data

Feb. 10, 1978 [CH] Switzerland .................. 1513/78

[51] Int. Cl.³ .............. B41M 5/16; B41M 5/18; B41M 5/22
[52] U.S. Cl. ............................ 282/27.5; 427/151; 428/307; 428/537; 428/913; 428/914
[58] Field of Search ............ 106/21; 260/315, 326.85, 260/326.13 H, 343.3 R; 282/27.5; 427/150, 151; 428/307, 411, 537, 913, 914; 544/60-62, 128, 142, 143, 151, 153, 376; 546/152, 186, 201

[56] References Cited

U.S. PATENT DOCUMENTS

| | | | |
|---|---|---|---|
| 2,861,082 | 11/1958 | Wheeler et al. | 260/343.3 R |
| 2,886,576 | 5/1959 | Wheeler et al. | 260/343.3 R |
| 2,945,865 | 7/1960 | Wheeler et al. | 260/343.3 R |
| 2,997,481 | 8/1961 | Wheeler et al. | 260/343.3 R |
| 4,055,358 | 10/1977 | Garner et al. | 282/27.5 |
| 4,189,171 | 2/1980 | Crounse et al. | 282/27.5 |
| 4,191,690 | 3/1980 | Burri | 260/343.3 R |
| 4,200,313 | 4/1980 | Schmidt et al. | 282/27.5 |

FOREIGN PATENT DOCUMENTS

46-4616 2/1971 Japan .................. 260/343.3 R

OTHER PUBLICATIONS

Miyazawa et al., Chem. Abstracts, vol. 85, 1976, p. 22774n.

*Primary Examiner*—Bruce H. Hess
*Attorney, Agent, or Firm*—Edward McC. Roberts; John P. Spitals

[57] ABSTRACT

Substituted 3,6-diaminophthalides of the formula

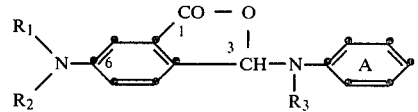

wherein each of $R_1$, $R_2$ and $R_3$ independently represents alkyl of not more than 12 carbon atoms which is unsubstituted or substituted by halogen, hydroxyl, cyano or lower alkoxy, or represents cycloalkyl, benzyl, or benzyl which is substituted by halogen, lower alkyl or lower alkoxy, and $R_1$ can also be hydrogen and $R_3$ can also be phenyl, or $R_1$ and $R_2$, together with the nitrogen atom to which they are attached, represent a 5- or 6-membered heterocyclic radical and the ring A is unsubstituted or substituted or contains a fused, unsubstituted or substituted benzene or heterocyclic ring.

These compounds are suitable in particular for use as color formers in pressure-sensitive or heat-sensitive recording materials.

6 Claims, No Drawings

RECORDING MATERIAL EMPLOYING SUBSTITUTED 3,6-DIAMINOPHTHALIDES AS COLOR FORMERS

This is a Divisional of application Ser. No. 942,840, filed on Sept. 15, 1978, now U.S. Pat. No. 4,191,690.

The present invention relates to novel substituted 3,6-diaminophthalides, a process for their production and the use thereof as colour formers in pressure-sensitive or heat-sensitive recording material.

The novel substituted diaminophthalides have the general formula

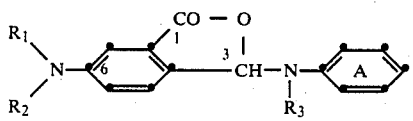
(1)

wherein each of $R_1$, $R_2$ and $R_3$ independently represents alkyl of not more than 12 carbon atoms which is unsubstituted or substituted by halogen, hydroxyl, cyano or lower alkoxy, or represents cycloalkyl, benzyl, or benzyl which is substituted by halogen, lower alkyl or lower alkoxy, and $R_1$ can also be hydrogen and $R_3$ can also be phenyl, or $R_1$ and $R_2$, together with the nitrogen atom to which they are attached, represent a preferably saturated, heterocyclic radical having 5 or 6 members, and the ring A is unsubstituted or substituted by halogen, nitro, cyano, trifluoromethyl, lower alkyl, lower alkoxy, lower alkoxycarbonyl, aryl, aryloxy, di-(lower alkyl)amino, acyl or acylamino, each containing 1 to 9 carbon atoms, arylamino, diarylamino, N-lower alkyl-N-arylamino, di-(lower alkyl)aminosulfonyl, di-(lower alkyl)aminocarbonyl, arylaminosulfonyl or arylaminocarbonyl, or contains a fused, unsubstituted or substituted benzene or heterocyclic ring.

In the definition of the radicals of the diaminophthalides, lower alkyl and lower alkoxy usually denote those groups or group components which contain 1 to 5, especially 1 to 3, carbon atoms, for example methyl, ethyl, m-propyl, isopropyl, n-butyl, sec-butyl, tert-butyl or amyl, and methoxy, ethoxy or isopropoxy.

The term "aryl" comprises preferably phenyl. The acyl radical is in particular lower alkylcarbonyl, for example formyl, acetyl, propionyl and benzoyl. Further acyl radicals are lower alkylsulfonyl, for example methylsulfonyl or ethylsulfonyl and also phenylsulfonyl. Phenyl, benzoyl and phenylsulfonyl can be substituted by halogen, methyl, methoxy or ethoxy.

Alkyl groups represented by $R_1$, $R_2$ and $R_3$ can be straight chain or branched. Examples of such alkyl radicals are: methyl, ethyl, n-propyl, isopropyl, n-butyl, sec-butyl, n-hexyl, n-octyl or n-dodecyl.

Substituted alkyl radicals $R_1$ and $R_2$ are in particular cyanoalkyl, haloalkyl, hydroxyalkyl, alkoxyalkyl, each containing 2 to 4 carbon atoms, for example β-cyanoethyl, β-chloroethyl, β-hydroxyethyl, β-methoxyethyl or β-ethoxyethyl.

Cycloalkyl represented by $R_1$, $R_2$ and $R_3$ is for example cyclopentyl or, preferably, cyclohexyl.

Preferred substituents in the benzyl group represented by $R_1$, $R_2$ and $R_3$ are for example halogen, methyl or methoxy. Examples of such araliphatic radicals are p-methylbenzyl, o- or p-chlorobenzyl, or o- or p-methoxybenzyl.

A heterocyclic radical represented by $R_1$ and $R_2$ together with the nitrogen atom to which they are attached is for example pyrrolidino, piperidino, pipecolino, morpholino, thiomorpholino or piperazino.

$R_1$ and $R_2$ can be different from each other or they are preferably indentical. $R_1$ and $R_2$ are preferably benzyl or lower alkyl. $R_3$ is advantageously alkyl of not more than 12 carbon atoms which is unsubstituted or substituted by halogen, hydroxyl, cyano or lower alkoxy, or is cycloalkyl, benzyl, or benzyl which is substituted by halogen, lower alkyl or lower alkoxy. $R_3$ is in particular lower alkyl or benzyl.

The ring A is preferably substituted as defined herein. Advantageously, the ring A can be contain 1 or 2 substituents. Preferred substituents of the ring A are halogen, nitro, cyano, trifluoromethyl, lower alkyl, lower alkoxy, phenoxy, halophenoxy, di-lower alkylamino, lower alkylcarbonylamino, benzoylamino, lower alkoxycarbonyl or fused, unsubstituted or substituted benzene or heterocyclic rings. If the ring A contains a fused heterocyclic ring, it forms for example a substituted or unsubstituted indolyl, benzothiazolyl, cumarin, quinoline or carbazolyl radical. The fused benzene or heterocyclic rings can be substituted in particular by halogen, cyano, nitro, lower alkyl or lower alkoxy. Most preferably, the ring A contains halogen, lower alkyl, lower alkoxy or phenoxy.

Preferred substituted diaminophthalides are those of the formula

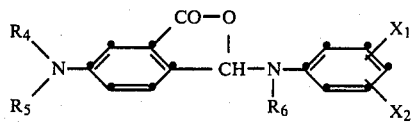
(2)

wherein each of $R_4$, $R_5$ and $R_6$ independently represents lower alkyl or benzyl, or $R_4$ and $R_5$ together with the nitrogen atom to which they are attached, represent a saturated heterocyclic radical having 5 or 6 members, $X_1$ represents halogen, lower alkyl, lower alkoxy, di-(lower alkyl)amino, phenoxy, halophenoxy or lower alkylcarbonylamino, and $X_2$ represents hydrogen, halogen, lower alkyl or lower alkoxy.

The most preferred colour formers are substituted 3,6-diaminophthalides of the formula

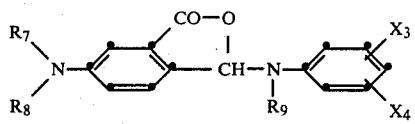
(3)

wherein each of $R_7$, $R_8$ and $R_9$ independently represents lower alkyl, $X_3$ represents halogen, lower alkyl, lower alkoxy or phenoxy, and $X_4$ represents hydrogen, halogen, lower alkyl or lower alkoxy.

Particularly preferred diaminophthalides of the formula (3) are those wherein each of $R_7$, $R_8$ and $R_9$ independently represents methyl or ethyl, $X_3$ represents halogen, lower alkyl or lower alkoxy, and $X_4$ represents hydrogen, halogen, methyl or methoxy.

Halogen in connection with the above substituents in the formulae (1), (2) and (3) is for example fluorine, bromine or preferably chlorine.

The substituted diaminophthalides of the present invention are obtained by reacting an aminophthaldehyde acid of the formula

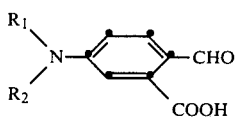

(4)

in which $R_1$ and $R_2$ have the given meanings, with an amino compound of the formula

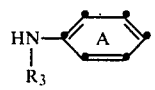

(5)

wherein A and $R_3$ have the given meanings.

The reaction is preferably carried out in an organic solvent and at reflux temperature. Basic condensation agents, for example nitrogen bases, such as pyridine, can be used concurrently.

Examples of suitable solvents are: cycloaliphatic or aromatic hydrocarbons, for example cyclohexane, benzene, toluene, xylene or tetrahydronaphthalene; chlorinated hydrocarbons, for example chloroform, carbon tetrachloride, ethylene chloride or chlorobenzenes; lower aliphatic alcohols, for example methanol, ethanol or isopropanol; ethers, such as dioxan, diethyl ether, glycol dimethyl ether or tetrahydrofuran.

The concentration of the reactants is not critical; however, it is advantageous to use one molar equivalent of each of the reactants. If desired, the reaction product of the formula (1) can be purified by recrystallisation from an organic solvent.

The aminophthaldehyde acids of the formula (4) are described in German Offenlegungsschrift No. 2,643,569. They can be obtained by saponification of the corresponding acid esters or by reaction of an aminobenzoic anhydride with formamides in the presence of an acid halide.

The substituted phthalide compounds of the formulae (1) to (3) are normally colourless or faintly coloured. When these colour formers are brought into contact with an acid developer, i.e. an electron acceptor, they produce intense yellow, orange or red shades of excellent light-fastness. They are therefore also very useful when mixed with one or more other known colour formers, for example 3,3-(bis-aminophenyl)-phthalides, 3,3-(bis-indolyl)-phthalides, 2,6-diaminofluoranes or spiropyranes in order to give blue, navy blue, grey or black colourations.

The phthalide compounds of the formulae (1) to (3) exhibit both on clay and on phenolic substrates an improved colour intensity and lightfastness. They are suitable in particular as rapidly developing colour formers for use in a pressure-sensitive or heat-sensitive recording material, which can be both copying and documenting material.

A pressure-sensitive material consists for example of at least one pair of sheets, which contain at least one colour former of the formulae (1) to (3), dissolved in an organic solvent, and a solid electron acceptor as developer. The colour former effects a coloured marking at those points where it comes into contact with the electron acceptor.

Typical examples of such developers are attapulgite clay, acid-activated bentonite (silton clay), silica, bentonite, zeolite, montmorillonite, halloysite, aluminum oxide, aluminum sulphate, aluminum phosphate, zinc chloride, kaolin or clays or organic compounds with acid reaction, for example unsubstituted or ring-substituted phenols, salicyclic acid or esters of salicyclic acid and the metal salts thereof, and also an acid polymeric material, for example a phenolic polymer, an alkylphenolacetylene resin, a maleic acid/colophonium resin or a partially or completely hydrolysed polymer of maleic acid and styrene, ethylene or vinyl methyl ether, or carboxypolymethylene. Preferred developers are attapulgite clay, silton clay or phenolformaldehyde resins. These electron acceptors are preferably applied in the form of a layer to the face of the receiver sheet.

In order to prevent the colour formers contained in the pressure-sensitive recording material from becoming prematurely active, they are usually separated from the electron acceptor. This can advantageously be accomplished by incorporating the colour formers in foam-like, sponge-like or honeycomb-like structures. Preferably, however, the colour formers are enclosed in microcapsules, which usually can be ruptured by pressure.

When the capsules are ruptured by pressure, for example with a pencil, and the colour former solution is transferred to an adjacent sheet which is coated with an electron acceptor, a coloured area is formed. This colour is produced by the resulting dye, which is absorbed in the visible range of the electromagnetic spectrum.

The colour formers are encapsulated preferably in the form of solutions in organic solvents. Examples of suitable solvents are preferably non-volatile solvents, for example polyhalogenated paraffin or diphenyl, such as trichlorodiphenyl or a mixture thereof with liquid paraffin; tricresyl phosphate, di-n-butyl phthalate, dioctyl phthalate, trichlorobenzene, nitrobenzene, trichloroethyl phosphate, hydrocarbon oils, such as paraffin, alkylated derivatives of naphthalene or diphenyl, terphenyls, partially hydrogenated terphenyl, or other chlorinated or hydrogenated condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457. The capsules can also be formed preferably from an aminoplast or from modified aminoplasts by polycondensation, as described in British Pat. Nos. 989,264; 1,156,725; 1,301,052 and 1,355,124.

The microcapsules containing the colour formers of formula (1) can be used for the production of a wide variety of known kinds of pressure-sensitive copying material. The various systems differ substantially from one another in the arrangement of the capsules, the colour reactants and the carrier material.

A preferred arrangement is that in which the encapsulated colour former is present in the form of a layer on the back of a transfer sheet and the electron acceptor substance is present in the form of a layer on the face of a receiver sheet. However the components can also be used in the paper pulp.

Another arrangement of the constituents consists in the microcapsules which contain the colour former, and the developer, being in or on the same sheet in the form of one or more individual layers, or being present in the paper pulp.

Such pressure-sensitive copying materials are described, for example, in U.S. Pat. Nos. 2,730,457; 2,932,582; 3,418,250; 3,427,180 and 3,516,846. Further systems are described in British Pat. Nos. 1,042,596;

1,042,597; 1,042,598; 1,042,599 and 1,053,935. Microcapsules which contain the colour formers of formula (1) are suitable for each of these systems and for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

As paper, there are used not only normal papers made from cellulose fibres, but also papers in which the cellulose fibres are replaced (partially or completely) by synthetic polymer fibres.

The phthalide compounds of the formulae (1) to (3) can also be used as colour formers in a thermoreactive recording material. This recording material usually contains at least one carrier, one colour former, one solid electron acceptor and optionally also at least one binder. Thermoreactive recording systems comprise for example heat sensitive recording and copying materials and papers. These systems are used, for example, for recording information, e.g. in electronic computers, teleprinters, telewriters, or in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor at those points where heat is applied and the desired colour develops at once.

The developers are the same electron-accepting substances as are used in pressure-sensitive papers. Examples of developers are the acid clays and phenolic resins already mentioned, or also phenolic compounds, for example 4-tertbutylphenol, 4-phenylphenol, 4-hydroxydiphenyl ether, α-naphthol, β-naphthol, 4-hydroxymethyl benzoate, 4-hydroxyacetophenone, 2,2'-dihydroxydiphenyl, 4,4-isopropylidenediphenol, 4,4'-isopropylidene-bis-(2-methylphenyl), 4,4'-bis-(hydroxyphenyl)valeric acid, hydroquinone, pyrogallol, chloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the production of the thermoreactive recording material. These binders are normally water-soluble, whereas the phthalide compound and the developer are insoluble in water. The binder should be able to disperse and fix the colour former and the developer at room temperature. By applying heat, the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. A preferred arrangement, however, is one in which the colour former and the developer are contained in one layer in a water-soluble binder.

The thermoreactive layers can contain further additives. To improve the degree of whiteness, to facilitate the printing of papers, and to prevent the heated pen from sticking, these layers can contain, for example, talc, $TiO_2$, $ZnO$ and $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Examples, the percentages are by weight unless otherwise indicated.

EXAMPLE 1

19.3 g of 2-carboxy-4-dimethylamino-benzaldehyde (2-formyl-5-dimethylaminobenzoic acid) and 16.6 g of N-methyl-p-ethoxy-aniline are heated under reflux in 200 ml of toluene. After 5½ hours, all the water formed in the course of the reaction has been removed via a water separator. The solution is boiled with a small amount of animal charcoal and filtered, and the product crystallises out on the addition of 100 ml of petroleum ether. The precipitate is collected by filtration and dried in vauo at 60° C. affording 20.4 g of a compound of the formula

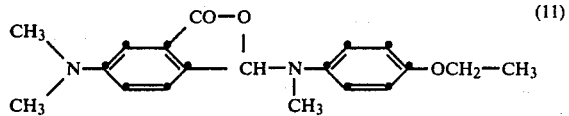

which melts at 135° to 136° C.

This colour former develops on silton clay a strong yellow colour of excellent lightfastness.

EXAMPLE 2

11.6 g of 2-carboxy-4-dimethylamino-benzaldehyde and 8.4 g of N-methyl-p-chloroaniline are heated to reflux in 250 ml of toluene. The water formed during the reaction is removed via a water separator. The reaction is complete after 16 hours. Then 200 ml of petroleum ether are added to the toluene solution, whereupon the product precipitates in crystalline form. The precipitate is collected by filtration and dried in vacuo at 60° C., affording 16.1 g of the colourless product of the formula

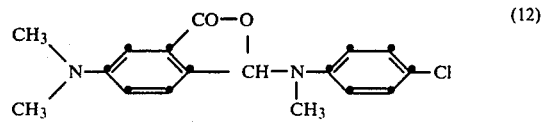

The compound has a melting point of 152° to 154° C. This colour former immediately develops on silton clay a strong yellow colour of excellent lightfastness.

EXAMPLE 3

11.6 g of 2-carboxy-4-dimethylamino-benzaldehyde and 7.3 g of N-methyl-p-toluidine are heated to reflux in 250 ml of toluene. After 16 hours, all the water formed during the reaction has been removed via a water separator. The toluene solution is diluted with 200 ml of petroleum ether, whereupon the product precipitates in crystalline form. The precipitate is collected by filtration and dried in vacuo at 60° C., affording 7 g of a colourless compound of the formula

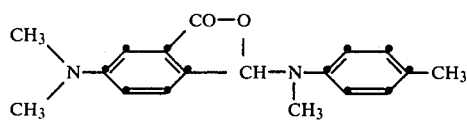
(13)

which melts at 135° to 137° C.

This colour former develops immediately on silton clay a strong yellow colour of excellent lightfastness.

The corresponding 3-(N-methyl-p-toluidino)-6-diethylaminophthalide compound, which also develops on silton clay a yellow colour of good lightfastness, is obtained by replacing the 2-carboxy-4-dimethylaminobenzaldehyde employed in this Example by an equimolar amount of 2-carboxy-4-diethylamino-benzaldehyde.

EXAMPLE 4

11.6 g of 2-carboxy-4-dimethylamino-benzaldehyde and 7.3 g of N-ethyl-m-toluidine are heated to reflux in 250 ml of toluene. After 16 hours, all the water which has formed during the reaction has been removed via a water separator. The toluene solution is diluted with 200 ml of petroleum ether, whereupon the product precipitates in crystalline form. The precipitate is collected by filtration and dried in vacuo at 60° C., affording 16.1 g of a colourless compound of the formula

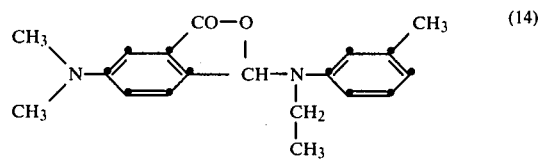
(14)

with a melting point of 138° to 139° C.

This colour former develops immediately on silton clay a strong yellow colour of excellent lightfastness.

The colour formers of the formula

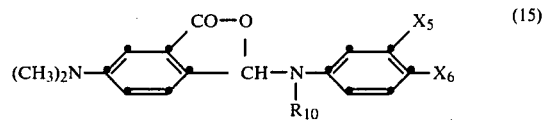
(15)

listed in the following table are obtained in the same manner as described in Example 1.

TABLE

| Example | $R_{10}$ | $X_5$ | $X_6$ | m.p. in °C. | Colour on silton clay |
|---|---|---|---|---|---|
| 5 | $CH_3$ | H | $-O-\phi$ | 125–126 | greenish yellow |
| 6 | $CH_3$ | H | $-N(CH_3)_2$ | 142–144 | orange red |
| 7 | $CH_3$ | $CF_3$ | H | 137–139 | greenish yellow |
| 8 | $CH_3$ | H | $NO_2$ | 244–246 | yellow |
| 9 | $CH_3$ | Cl | Cl | 180–183 | yellow |
| 10 | $CH_3$ | H | Br | 152–154 | yellow |
| 11 | $CH_3$ | $-OCH_3$ | $-OCH_3$ | 139–142 | yellow |
| 12 | $-CH_2-\phi$ | H | Cl | 144–149 | yellow |
| 13 | $-CH_2-CH_3$ | H | Cl | 140–142 | yellow |

EXAMPLE 14

6.4 g of 2-carboxy-4-dimethylamino-benzaldehyde and 3.9 g of N-methylaniline are heated to reflux in 150 ml of benzene. The water which has formed during the reaction is removed via a water separator. After 8 hours, 50 ml of benzene are distilled off and the reaction solution is cooled, whereupon the colourless product crystallises out. The precipitate is collected by filtration and dried in vacuo at 60° C., affording 7.1 g of the compound of the formula

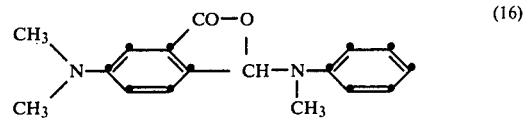
(16)

which melts at 152° C.

This colour former develops immediately on silton clay a greenish yellow colour of excellent lightfastness.

EXAMPLE 15

Production of a pressure-sensitive copying paper

A solution of 3 g of the phthalide compound of the formula (11) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resulting emulsion is poured into 600 g of ice water, whereupon the coacervation is effected. A sheet of paper is coated with the resulting suspension of microcapsules and dried. A second sheet of paper is coated with silton clay. The first sheet and the sheet of paper coated with silton clay are laid on top of each other with the coated sides face to face.

Pressure is exerted on the first sheet by writing by hand or typewriter and an intense yellow copy of excellent lightfastness develops on the sheet which is coated with clay.

Intense, lightfast yellow copies can also be obtained by using the colour formers of the formulae (12) to (16) given in Examples 2 to 14 instead of the phthalide compound of the formula (11).

EXAMPLE 16

Production of a thermoreactive paper 6 g of an aqueous dispersion which contains 1.57% of the phthalide compound of the formula (11) and 6.7% of polyvinyl alcohol are mixed with 134 g of an aqueous dispersion which contains 14% of 4,4-isopropylidenediphenol, 8% of attapulgite clay and 6% of polyvinyl alcohol. This mixture is applied to a paper and dried. Contacting the paper with a heated ball-point pen produces a yellow colour of excellent lightfastness.

Intense yellow colours can also be obtained by using each of the other colour formers of Examples 2 to 14.

What is claimed is:

1. A pressure-sensitive or heat-sensitive recording material containing a support coated with the color forming 3,6-diaminophthalide of the formula

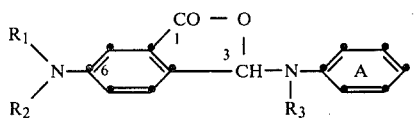

(1)

wherein $R_1$ represents hydrogen, alkyl of not more than 12 carbon atoms which is unsubstituted or substituted by halogen, hydroxyl, cyano or lower alkoxy, or represents cycloalkyl, benzyl, or benzyl which is substituted by halogen, lower alkyl or lower alkoxy, $R_2$ represents alkyl of not more than 12 carbon atoms which is unsubstituted or substituted by halogen, hydroxyl, cyano or lower alkoxy, or represents cycloalkyl, benzyl, or benzyl which is substituted by halogen, lower alkyl or lower alkoxy and $R_3$ represents alkyl of not more than 12 carbon atoms which is unsubstituted or substituted by halogen, hydroxyl, cyano or lower alkoxy, or represents cycloalkyl, phenyl, benzyl, or benzyl which is substituted by halogen, lower alkyl or lower alkoxy, or $R_1$ and $R_2$, together with the nitrogen atom to which they are attached, represent a 5- or 6-membered heterocyclic radical and the ring A is unsubstituted or substituted by halogen, nitro, cyano, trifluoromethyl, lower alkyl, lower alkoxy, lower alkoxycarbonyl, aryl, aryloxy, di-(lower alkyl)amino, acyl or acylamino, each acyl containing 1 to 9 carbon atoms, arylamino, diarylamino, N-lower alkyl-N-arylamino, di-(lower alkyl)aminosulfonyl, di-(lower alkyl)aminocarbonyl, arylaminosulfonyl or arylaminocarbonyl, or contains a fused, unsubstituted or substituted benzene or heterocyclic ring.

2. A pressure-sensitive recording material according to claim 1, which contains as colour former at least one phthalide of the formula as indicated in claim 1, dissolved in an organic solvent, and at least one solid electron acceptor.

3. A pressure-sensitive recording material according to claim 2, wherein the phthalide compound is encapsulated in micro-capsules.

4. A pressure-sensitive recording material according to claim 3, wherein the encapsulated phthalide compound is applied in the form of a layer to the back of a transfer sheet and the electron acceptor is applied in the form of a layer to the face of a receiver sheet.

5. A heat-sensitive recording material according to claim 1, which contains in at least one layer, at least one said colour former, at least one solid electron acceptor and at least one binder.

6. A heat-sensitive recording material according to claim 5 which contains at least one phthalide compound as the colour former and at least one electron acceptor in at least one binder layer on paper.

* * * * *